United States Patent [19]
Garcia-Olmedo et al.

[11] Patent Number: 6,147,281
[45] Date of Patent: Nov. 14, 2000

[54] ANTIPATHOGENIC PEPTIDES AND COMPOSITIONS CONTAINING SAME

[75] Inventors: Francisco Garcia-Olmedo; Antonio Molina Fernandez, both of Madrid, Spain

[73] Assignee: Universidad Politecnia de Madrid, Madrid, Spain

[21] Appl. No.: 08/404,607

[22] Filed: Mar. 15, 1995

Related U.S. Application Data

[62] Division of application No. 08/326,352, Oct. 20, 1994, Pat. No. 5,446,127, which is a continuation of application No. 07/965,284, Jan. 25, 1993, abandoned, which is a continuation of application No. PCT/EP92/01130, May 21, 1992.

[30] Foreign Application Priority Data

May 24, 1991 [ES] Spain ..................................... 9101258

[51] Int. Cl.$^7$ .............................. A01H 5/00; C12N 15/82
[52] U.S. Cl. ......................... 800/301; 800/279; 800/298; 435/418; 435/419; 435/320.1; 536/23.6
[58] Field of Search ..................................... 800/205, 298, 800/279, 301; 435/69.1, 172.3, 240.4, 320.1, 418, 419; 536/23.6; 530/300, 324, 370; 514/2

[56] References Cited

U.S. PATENT DOCUMENTS

| 4,940,840 | 7/1990 | Suslow et al. ......................... | 800/205 |
|---|---|---|---|
| 5,446,127 | 8/1995 | Garcia-Olmedo ....................... | 530/300 |

OTHER PUBLICATIONS

Swiss–Prot sequence entry NLT1–ORYSA, 1991.
Garcia–Olmedo et al., J. Exp. Botany, "Trysin/alpha–amylase Inhibitors and Thionins From Cereals: Possible Role In Crop Protection", vol. 42, 1991, 238 Suppl., Meeting Apr. 7–12, 1991.
Arondel et al., Exprientia, "Lipid Transfer in Plants", vol. 46 1990, pp. 579–585.
Bernhard et al., Archives of Biochemistry and Biophysics, "Coidentity of Putative Amylase Inhibitors From Barley and Finger Millet with Phospholipid Transfer Proteins Inferred From Amino Acid Sequence Homology", vol. 269, No. 2, Mar. 1989, pp. 695–697.
Tchang et al., J. Biological Chemistry, "Phospholipid Transfer Protein: Full–length cDNA and Amino Acid Sequence in Maize", vol. 263, No. 32, Nov. 15, 1988, pp. 16849–16855.
Biological Abstract BR41:82577.
Mundy et al., "Selective Expression of a Probable Amylase/Protease Inhibitor in Barley Aleurone Cells: Comparison to the Barley Amylase/Subtilisin Inhibitor", (1986) Planta 169: pp. 51–63.
Lewin (1987) Science 237:1570.
Ebrahim–Nesbat et al., "Cultivar–Related Differences in the Districution of Cell–Wall–Bound Thionins in Compatible and Incompatible Interactions Between Barley and Powdery Mildew", (1989) Planta 179: pp. 203–210.
Lamb et al., "Signals and Transduction Mechanisms for Activation of Plant Defenses Against Microbial Attack", (1989) Cell 56: pp. 215–224.

*Primary Examiner*—Elizabeth F. McElwain
*Attorney, Agent, or Firm*—Wenderoth, Lind & Ponack, LLP.

[57] ABSTRACT

The present invention relates to novel antipathogenic peptides, to DNA sequences encoding said peptides, to vectors comprising said DNA sequences, to transgenic plants comprising a DNA sequence encoding said peptides, to compositions containing anti-pathogenic peptides and to the use of said peptides and compositions for controlling plant pathogens, Also comprised are methods of preparing antipathogenic peptides or compositions containing same and transgenic plants able to synthesize anti-pathogenically effective amounts of said peptides.

23 Claims, 1 Drawing Sheet

- α1/β-Thionin [wheat endosperm]
- △ LT26-Thionin [barley leaf]
- ■ CW21
- ○ CW18

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ala Ile Thr Cys Gly Gln Val Ser Ser Ala Leu
1               5                   10

(2) INFORMATION FOR SEQ ID NO:2:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Ala Ile Ser Cys Gly Gln Val Ser Ser Ala Leu Ser Pro Cys
1               5                   10

Ile Ser Tyr Ala Arg Gly Asn Gly Ala
15              20

(2) INFORMATION FOR SEQ ID NO:3:

(i) SEQUENCE CHARACTERISTICS:
      (A) LENGTH: 90 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Ala Ile Thr Cys Gly Gln Val Ser Ser Ala Leu Gly Pro Cys
1               5                   10

Ala Ala Tyr Ala Lys Gly Ser Gly Thr Ser Pro Ser Ala Gly
15              20                  25

Cys Cys Ser Gly Val Lys Arg Leu Ala Gly Leu Ala Arg Ser
                30              35              40

Thr Ala Asp Lys Gln Ala Thr Cys Arg Cys Leu Lys Ser Val
            45              50              55

Ala Gly Ala Tyr Asn Ala Gly Arg Ala Ala Gly Ile Pro Ser
            60              65              70

-continued

Arg Cys Gly Val Ser Val Pro Tyr Thr Ile Ser Ala Ser Val
                75                  80

Asp Cys Ser Lys Ile His
85                  90

(2) INFORMATION FOR SEQ ID NO:4:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Ile Ser Cys Gly Gln Val Ser Ser Ala Leu Ser Pro Cys
1               5                   10

Ile Ser Tyr Ala Arg Gly Asn Gly Ala Lys Pro Pro Ala Ala
15                  20                  25

Cys Cys Ser Gly Val Lys Arg Leu Ala Gly Ala Ala Gln Ser
        30                  35                  40

Thr Ala Asp Lys Gln Ala Ala Cys Lys Cys Ile Lys Ser Ala
            45                  50                  55

Ala Gly Gly Leu Asn Ala Gly Lys Ala Ala Gly Ile Pro Ser
                60                  65                  70

Met Cys Gly Val Ser Val Pro Tyr Ala Ile Ser Ala Ser Val
                75                  80

Asp Cys Ser Lys Ile Arg
85                  90

(2) INFORMATION FOR SEQ ID NO:5:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ala Ile Thr Cys Gly Gln Val Ser Ser Ala Leu Gly Pro Cys
1               5                   10

Ala Ala Tyr Ala Lys Gly Ala Gly Val Asn Pro Ser Ala Gly
15                  20                  25

Cys Cys Ser Gly Val Lys Arg Leu Ala Gly Leu Ala Arg Ser
        30                  35                  40

Thr Ala Asp Lys Gln Ala Thr Cys Arg Cys Leu Lys Ser Val
            45                  50                  55

Ala Gly Ala Tyr Asn Ala Gly Arg Ala Ala Gly Ile Pro Ser
                60                  65                  70

Arg Cys Gly Val Ser Val Pro Tyr Thr Ile Ser Ala Ser Val
                75                  80

Asp Cys Ser Lys Ile His
85                  90

(2) INFORMATION FOR SEQ ID NO:6:

(i) SEQUENCE CHARACTERISTICS:
        (A) LENGTH: 23 amino acids

```
        (B) TYPE:  amino acid
        (C) STRANDEDNESS:  single
        (D) TOPOLOGY:  linear (ii) MOLECULE TYPE:  peptide (xi) SEQUENCE DESCRIPTION: SEQ ID NO:6:

Ala Ile Ser Cys Gly Gln Val Ser Ser Ala Leu Ser Pro Cys
1               5                   10

Ile Ser Tyr Ala Arg Gly Asn Asn Ala
15                  20
```

ANTIPATHOGENIC PEPTIDES AND COMPOSITIONS CONTAINING SAME

This is a divisional application of Ser. No. 08/326,352, filed Oct. 20, 1994, now U.S. Pat. No. 5,446,127 which was a continuation of application Ser. No. 07/965,284 filed Jan. 25, 1993, now abandoned, which is a continuation of PCT/EP92/01130, filed May 21, 1992.

BACKGROUND OF THE INVENTION

1. Field of the Invention

The present invention relates to novel antipathogenic peptides, to DNA sequences encoding said peptides, to vectors comprising said DNA sequences, to transgenic plants comprising a DNA sequence encoding said peptides, to compositions containing anti-pathogenic peptides and to the use of said peptides and compositions for controlling plant pathogens. Also comprised are methods of preparing antipathogenic peptides or compositions containing same and transgenic plants able to synthesize anti-pathogenically effective amounts of said peptides.

2. Description of Related Art

Peptides showing antipathogenic and especially antimicrobial activity are already known in the art. Specifically of importance are the so-called lytic peptides, some of which are known to be active against a broad range of organisms while others produce little or no effect There are many examples of lytic peptides from animal, plant, insect and microbial sources including the mammalian defensins, cecropins, thionins, mellitins, insect defensins, magainins, attacins, dipterins, sapecins, caerulins, xenopsins, or hybrids thereof. The amino acid sequence of several lytic peptides with antimicrobial activity are disclosed in WO 89/04371. Lehrer et al. (1986) disclose six antimicrobial peptides (AMPs) from rabbit granulocytes that are structurally homologous to human neutrophil defensins. Three of the rabbit AMPs (NP-1, NP-2 and NP-3a) are disclosed to be effective against *Candida albicans*.

Another class of peptides with antipathogenic activity is represented by hydrolytic enzymes, such as chitinase and β-1,3-glucanase, which are known to inhibit fungal growth (Schlumbaum et al., 1986; Mauch et al., 1988).

SUMMARY OF THE INVENTION

The present invention provides a further class of peptides which were found to be active against a broad range of pathogens affecting plants. This class of peptides embraces known as well as novel representatives. These peptides are especially suited for use in an antipathogenic composition for controlling plant pathogens.

It is, therefore, one of the objects of the present invention to provide an antipathogenic composition for controlling plant pathogens comprising together with a suitable carrier customarily used in agricultural peptide formulations an antipathogenically effective amount of a peptide according to the present invention.

It is another object of the invention to provide a method of protecting plants from the attack of plant pathogens, preferably from the attack of pathogenic bacteria and/or fungi, and most preferably from the attack of pathogenic bacteria, which comprises applying an antipathogenically effective amount of a peptide according to the invention or an anti-pathogenic composition containing said peptide to the plant or to the plant pathogen's habitat.

It is another object of the invention to provide novel antipathogenic peptides that can be used as active ingredients in a composition according to the invention.

It is a further object of the invention to provide methods of preparing an antipathogenic peptide according to the invention and a composition containing said peptide.

It is a further object of the present invention to provide transgenic plants with anti-pathogenic effective activity based on the expression of one or more inventive peptides in the plant cells.

It is another object of the present invention to provide transgenic plants that contain DNA sequences coding for the inventive peptides.

DETAILED DESCRIPTION OF THE PREFERRED EMBODIMENT(S)

Figure 1:
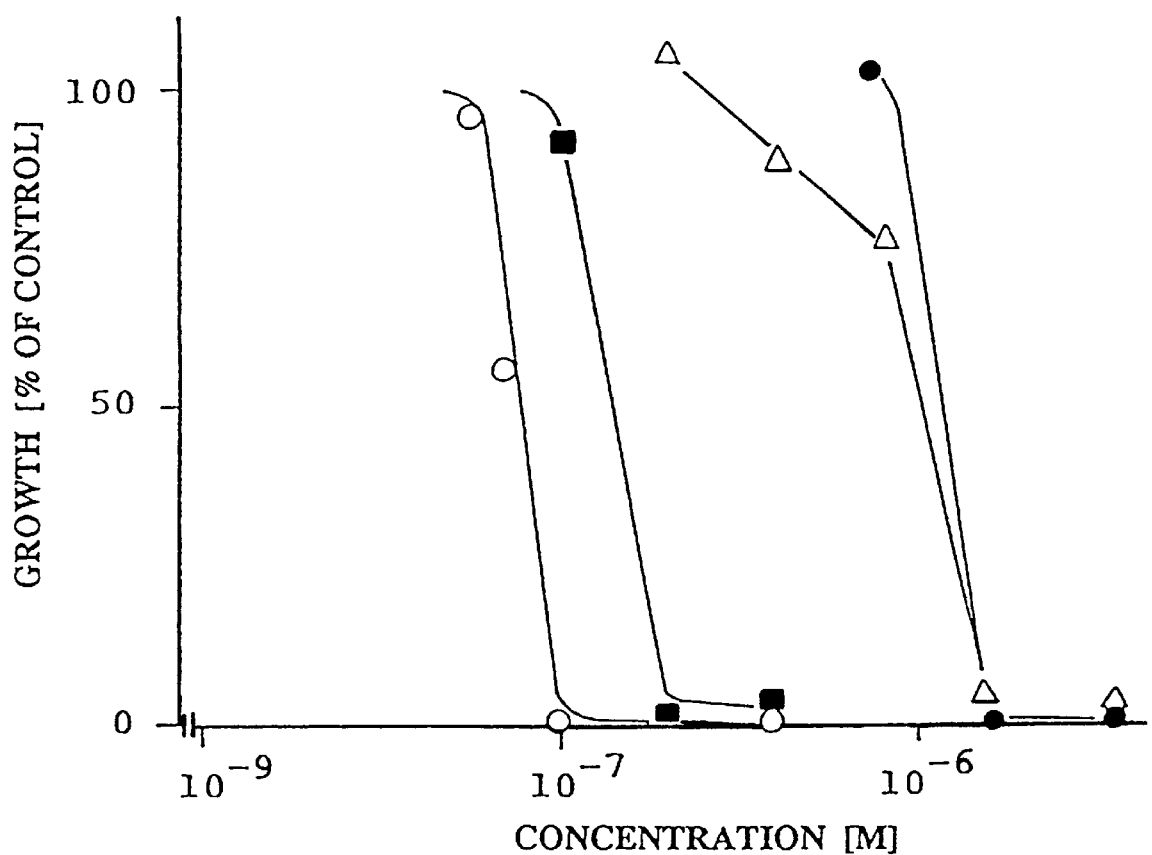
FIG. 1 shows the results of an antibacterial assay employing two of the peptides of this invention.

The peptides that can be used according to the present invention are characterized in that they contain at their N-terminal end a hydrophobic region which preferably comprises one of the following amino acid sequences:
(a) SEQ ID NO:1; or
(b) SEQ ID NO:2; or
(c) SEQ ID NO:6; or
(d) an N-terminal amino acid sequence that is substantially homologous to at least one of the above sequences.

The peptides of the present invention can be obtained from many sources, including but not limited to microbes, fungi, plants and even higher animals. They can be obtained from the cell wall, the cell membrane and the cytosolic fraction.

Peptides which possess an amino acid sequence at their N-terminal end that is substantially homologous to the N-terminal sequences disclosed above and thus may be used according to the invention, include, for example, phospholipid transfer proteins, for example, phospholipid transfer proteins from maize (Tchang et al., 1988; Sossountzov et al., 1991), spinach (Bouillon et al., 1987; Bernhard et al., 1991), tomato (Torres-Schumann et al., 1992), plants and microorganisms (Yamada, 1992), carrot (Sterk et al., 1991), ragi (Campos and Richardson, 1984), and Ricinus (Takishima et al., 1986). A further example would be a small polypeptide isolated from the aleurone cells of barley and millet, which have been previously identified as putative amylase/protease inhibitors (Mundy and Rogers, 1986; Svensson et al., 1986; Bernhard et al., 1989).

However, preferred within the scope of the present invention are peptides which can be preferably obtained from leaves of etiolated barley plants and are characterized by the following features:
(a) an apparent molecular weight within the range of about 5 kD to 12 kD;
(b) a retention time in HPLC purification of 96.30 and 106.30 min., respectively;
(c) an amino acid composition as given in table 1 below;
(d) a hydrophobic N-terminal sequence preferably comprising one of the following amino acid sequences:
($d_1$) SEQ ID NO:1; or
($d_2$) SEQ ID NO:2; or
($d_3$) SEQ ID NO:6; or
(e) an antimicrobial activity, especially against *Corynebacterium sepedonicum*.

It goes without saying that the peptides of the present invention can be obtained from further sources, for example, also from the cytosolic fraction and not only from leaves of etiolated plants.

Also useful as peptides of the present invention are synthetic peptides, which may be functional derivatives of one of the peptides above or functional hybrids thereof.

Most preferred is a peptide having the amino acid sequence SEQ ID NO:3 or SEQ ID NO:4 or SEQ ID NO:5.

Surprisingly, it has been found that the peptides described above have for practical purposes a very advantageous microbicidal spectrum, especially against phytopathogenic bacteria and fungi. For example, said peptides have very advantageous curative, preventive and systemic phytotherapeutic properties and can be used for protecting cultivated plants. With these peptides it is possible to inhibit or kill the plant pathogens which occur in or on plants, or parts of plants.

Accordingly, the invention also relates to antipathogenic compositions comprising as an active component one or more of the peptides described above, containing at their N-terminal end a hydrophobic region which preferably comprises one of the following amino acid sequences:
(a) SEQ ID NO:1; or
(b) SEQ ID NO:2; or
(c) SEQ ID NO:6; or
(d) an N-terminal amino acid sequence that is substantially homologous to at least one of the above sequences,
in an antipathogenically effective amount, together with carriers and/or adjuvants customarily used in agricultural peptide formulations.

Most preferred is a composition comprising as an active component a peptide having the amino acid sequence SEQ ID NO:3 or SEQ ID NO:4 or SEQ ID NO:5.

An antipathogenic composition according to the invention comprises in addition to the active component an agriculturally acceptable carrier and/or an adjuvant referring to those substances, or a combination of substances, that are known in the art of agricultural compositions, and may include, where appropriate, one or more compounds selected from the group consisting of solid or liquid adjuvants, solvents, surfactants and other compounds normally used in agricultural formulations.

It is a further object of the present invention to provide an antipathogenic composition comprising together with a suitable carrier customarily used in agricultural peptide formulations, an anti-pathogenically effective amount of an active ingredient; wherein the active ingredient comprises a peptide according to the invention and a lytic peptide. Preferred are compositions wherein the components of the active ingredient are present in a synergistically effective amount.

It is a further object of the present invention to provide an antipathogenic composition comprising together with a suitable carrier customarily used in agricultural peptide formulations, an anti-pathogenically effective amount of an active ingredient; wherein the active ingredient comprises a phospholipotransfer protein and a lytic peptide. Preferred are compositions wherein the components of the active ingredient are present in a synergistically effective amount.

A preferred lytic peptide is a thionin.

As used in the present application, an "antipathogenically effective amount" of a substance or composition means an amount which will kill or inhibit the growth of the target plant pathogen when applied to a plant, or when expressed in a transgenic plant.

The term "plant pathogen" includes fungi, bacteria, nematodes and insects. The preferred target pathogens according to the present invention are bacteria and fungi. Especially preferred as target pathogens are bacteria.

As used in the present application, substantial sequence homology means close structural relationship between sequences of nucleotides or amino acids. For example, substantially homologous DNA sequences may be 60% homologous, preferably 80 and most preferably 90% or 95% homologous, or more, and substantially homologous amino acid sequences may preferably be 35%, more preferably 50%, most preferably more than 50% homologous. Homology also includes a relationship wherein one or several subsequences of nucleotides or amino acids are missing, or subsequences with additional nucleotides or amino acids are interdispersed.

The term "homology" as used herein not only embraces structural homology but also functional homology.

As used in the present application, the term "constitutive" refers to a peptide that is present at all times in a plant cell. The term "inducible" refers to a peptide that is present in the plant cell only when the plant is subjected to some stress condition or external stimulus and the production or presence of the peptide is thereby activated or increased.

Induction may be by chemical means, for example, chemicals known to act as inducers of pathogen related proteins in plants include ethylene, benzoic acid, salicylic acid, poly-acrylic acid and substituted derivatives thereof. Induction may also be by other physiological and physical means, such as by high or low temperatures, physical wounding or by any other known inductive means.

The peptides according to the present invention can be prepared from suitable plant parts, for example from parts of etiolated plants, especially of etiolated barley plants. To minimize damage or loss of protein, working at low temperature, preferably at 4° C., and avoiding excess exposure to oxygen is recommended. In addition, certain chemicals can be added to the various buffer solutions used in the purification procedure. These include, for example, protein stabilizers such as glycerol, a sulfhydryl reagent such as dithiothreitol to minimize oxidation of cystein residues, and a metal chelater such as EDTA to prevent exposure of the protein to heavy metal ions that might inactivate the protein. In order to avoid loss of protein due to degradation by proteases addition of a protease inhibitor is often beneficial.

The preparation of the peptides according to the invention can be accomplished by separation methods that are well known in the art, including precipitation, phase partitioning, chromatography, electrophoresis, centrifugation and ultra-filtration.

The precipitation step may include, for example, ammonium sulfate precipitation, acetone precipitation, polyethyleneimine [Polymin P] precipitation and isoelectric precipitation.

The phase partitioning may include, for example, use of polyethylene glycol. When appropriate mixtures of polyethylene glycol [PEG], salt, and water are mixed, a two-phase system occurs. The partitioning of a given protein between the two phases can be influenced by the salt and polymer concentrations, temperature, and the pH used.

Among the chromatography procedures known in the art, the following proved to be useful in designing a purification procedure: Ion exchange chromatography, hydrophobic chromatography, affinity chromatography, immobilized metal affinity [IMAC] chromatography, immunoaffinity chromatography, chromatofocussing chromatography, gel filtration chromatography and especially high performance liquid chromatography [HPLC], which allow either reverse phase fractionation, hydrophobic affinity chromatography, gel filtration chromatography, or ion exchange chromatography to be carried out at high pressure. The columns used in the purification process are preferably decreased or minimized by the presence of mild nonionic detergents, such as NP40, in the buffer solutions, to avoid losses of protein due to nonspecific adsorption to the column material.

In a preferred embodiment of the present invention coleoptiles or shoots of etiolated barley plants are removed and used as source material for the subsequent protein extraction. The plant material removed is first ground to powder with liquid nitrogen and then homogenized and extracted in a suitable buffer solution. One or more further extraction steps are followed by an extraction with a solution of high salt concentration for extracting cell wall and membrane proteins. The solid particles are spun down and the supernatant is retained and dialyzed against distilled water. Alternatively, the supernatant can be desalted by column chromatography or precipitated by ammonium sulfate. The final purification is achieved by HPLC.

The determination of the relative proportion of the amino acids in the amino acid composition of the peptides according to the invention can be carried out by using methods well know in the art such as, for example, post-column O-phtaldialdehyd derivatization (Benzon and Hare, 1975) or alternatively pre-column phenylisothiocyanat derivatization according to Bidlingmeyer et al. (1984) after total hydrolysis.

N-terminal amino acid sequencing can be achieved by standard procedures such as, for example, automated Edman degradation.

Based on this sequence information, oligonucleotide probes can easily be prepared that can be used for the identification and isolation of the corresponding gene encoding the peptide.

Since the genetic code is known to be degenerate, different codons can in the majority of cases be used for one and the same amino acid. Apart from a few exceptional cases, a particular amino acid sequence can as a rule be coded for by a whole series of oligonucleotides that are similar to one another. However, care must be taken to ensure that only one member of that series of oligonucleotides actually coincides with the corresponding sequence in the gene that is being sought In order to limit from the outset the number of possible oligonucleotides, the rules on the use of codons laid down by Lathe et al. (1985), which take account of the frequency with which a particular codon is actually used in eukaryotic cells, may, for example, be applied. In order to facilitate the detection of the desired gene the above-described DNA probe can be labelled with a suitable readily detectable group.

The present invention also relates to a DNA sequence coding for a peptide or a fragment or part of a peptide according to the invention and to vectors comprising said DNA sequence. The DNA sequence may be a synthetic DNA sequence prepared by methods well-known in the art.

Having isolated the gene encoding one of the peptides according to the invention from a suitable source such as, for example, a cDNA or a genomic DNA library, one can easily use this gene for preparing transgenic plants that are protected from the attack of plant pathogens upon expression of the introduced gene.

The present invention also relates to transgenic plants that contain DNA sequences coding for at least one of the inventive peptides.

The present invention also relates to a method of preparing a transgenic plant which is able to synthesize anti-pathogenically effective amounts of one or more peptides wherein the method comprises
a) preparing a transgenic plant comprising recombinant DNA sequences encoding one or more peptides; or
b) preparing two or more transgenic plants comprising recombinant DNA sequences encoding one or more peptides, and crossing said plants using conventional breeding techniques.

Preferably the method comprises preparing a first homozygous transgenic plant comprising a recombinant DNA sequence encoding a first peptide, preparing a second homozygous transgenic plant comprising a recombinant DNA sequence encoding a second peptide, preparing a third homozygous transgenic plant comprising a recombinant DNA sequence encoding a third peptide, and crossing the three homozygous plants using conventional breeding techniques.

In transgenic plants, the synthesis of the peptides may be induced by use of an inducible expression system comprising an inducible gene and an inducing regulator.

To become expressed in the plant cell the DNA sequence is preferably cloned into a suitable vector for plant transformation which preferably comprise one or more promoter or regulatory DNA sequences to promote expression of the coding DNA sequence in the transformed plant cell. Numerous plant expression cassettes and vectors are well known in the art. Promoterless constructs can also be introduced into the plants.

Suitable control sequences are those comprising promoter and 5' and 3' untranslated regulatory sequences that are functional in plants. These sequences may, independently, be derived from any source, such as, for example, virus, plant or bacterial genes. These promoters or regulatory sequences can be constitutive in nature or can be regulated in their patterns of expression. Such regulation may be temporal or spatial and include developmentally regulated promoters and inducible promoters. Proteins may be optionally expressed in the vacuole or extracellularly using methods well-known in the art (EP 462,065). Preferred promoters include promoters from the cauliflower mosaic virus, including the 35S and 19S promoters. Cauliflower mosaic virus (CaMV) has been characterized and described by Hohn et al. (1982). This description is incorporated herein by reference. Also preferred are the nopaline synthase, octopine synthase and mannopine synthase promoters.

The virus promoters and 5' and 3' untranslated sequences suitable for use are functional in plants and include, for example, plant viruses such as cauliflower mosaic virus.

CaMV is an unusual plant virus in that it contains double-stranded DNA. At least two CaMV transcriptional promoters are functional in plants, namely the 19S promoter, which results in transcription of gene VI of CaMV, and the 35S promoter. The 19S promoter and the 35S promoter are the preferred plant virus promoters for use in the present invention.

Examples of plant gene promoters and 5' and 3' untranslated regions suitable for use in the present invention also include those of the gene coding for the small subunit of ribulose bisphosphate carboxylase oxygenase, phosphoenol pyruvatecarboxylase, actin, pathogenesis-related proteins and chlorophyll a/b-binding protein. These plant gene regions may be isolated from plant cells in ways comparable to those described above for isolating the corresponding regions from CaMV (Morelli et al., 1985).

Suitable promoters and 5' and 3' untranslated regions from bacterial genes include those present in the T-DNA region of Agrobacterium plasmids. Some examples of suitable Agrobacterium plasmids include the Ti plasmid of *A. tumefaciens* and the Ri plasmid of *A. rhizogenes*. The Agrobacterium promoters and 5' and 3' untranslated regions useful in the present invention are, in particular, those present in the genes coding for octopine, mannopine and nopaline synthases. These sequences may be obtained by methods similar to those described above for isolating CaMV and plant promoters and untranslated sequences (Bevan et al., 1983).

In addition to a promoter, the chimeric genes of the present invention may preferably include further untranslated sequences at the 5' end, termed a leader sequence. Suitable leader sequences include leader sequences of various lengths isolated from the 35S CaMV gene (Pierce et al., 1987). The preferred leader sequences are those isolated from the 35S CaMV gene, having a length from about 50 to about 130 nucleotides.

It is also advantageous for the expressible DNA, but especially the structural gene that is to be inserted, to comprise a sequence that codes for an N-terminal signal peptide capable of functioning in the plant cell, or to be linked in the 5'-terminal region to such a sequence. That signal peptide is a transport signal that is found at the N-terminal end of proteins transported via the endomembrane system. This signal sequence ensures that said proteins first pass into the endoplasmic reticulum, where the signal peptide is split off proteolytically from the precursor protein as soon as it has fulfilled its function. By virtue of its specific function, this type of signal peptide sequence has been conserved to a high degree during evoluton in all living cells, irrespective of whether they are bacteria, yeasts, fungi, animals or plants.

Moreover, the DNA molecule may comprise further sections of sequence that code for peptide fragments which as a whole contribute towards improving the competence for admission into the vacuole, for example the propeptide fragment discovered by Matsuoka and Nakamura (1991) in the N-terminal extension of sporamine.

The recombinant DNA comprising the peptide-encoding DNA sequence can be introduced into the plant cell in a number of ways that are well known to those of skill in the art. For example, methods of transforming plant cells include sonication (Joesbo and Brunstedt, 1990), microinjection (Crossway et al., 1986; Neuhaus, 1987), electroporation (Riggs et al., 1986), electroporation of intact cells (Molina et al., 1992), Agrobacterium mediated transformation (Hinchee et al., 1988), silicon carbide fiber-mediated delivery (Kaeppler et al., 1990), direct gene transfer (Paszkowski et al., 1984), and ballistic particle acceleration using, for example, devices available from Agracetus, Inc., Madison, Wis. and Dupont, Inc., Wilmington, Del. [U.S. Pat. No. 4,945,050; McCabe et al., 1988; Weissinger et al., 1988; Sanford et al., 1987 (onion); Christou et al., 1988 (soybean); McCabe et al., 1988 (soybean); Datta et al., 1990 (rice); Klein et al., 1988 (maize); Klein et al., 1988 (maize); Klein et al., 1989 (maize); Fromm et al., 1990; Gordon-Kamm et al., 1990 (maize)].

One possible method for introducing genetic material into plant cells comprises, for example, bringing plant cells into contact with viruses or with Agrobacterium comprising the DNA to be introduced. This may be achieved by infecting sensitive plant cells or by co-cultivating protoplasts derived from plant cells. Within the scope of this invention, Cauliflower Mosaic Virus (CaMV) may be used as a vector for the insertion of the peptide-encoding DNA sequence according to the invention into a plant.

Another method of inserting the peptide-encoding DNA sequence into a cell makes use of the infection of the plant cell with *Agrobacterium tumefaciens* and/or *Agrobacterium rhizogenes*, which has previously been transformed with said gene construction. The transgenic plant cells are then cultured under suitable culture conditions known to the person skilled in the art, so that they form shoots and roots, and whole plants are finally formed.

A further possible method of transforming plant material comprises mixed infection using both *Agrobacterium rhizogenes* and transformed *Agrobacterium tumefaciens*, as described by Petit et al. (1986) for the transformation of carrots.

The peptide-encoding DNA sequence according to the invention can therefore be transferred into suitable plant cells by means of, for example, the Ti-plasmid of *Agrobacterium tumefaciens* or the Ri-plasmid of *Agrobacterium rhizogenes*. The Ti-plasmid or Ri-plasmid is transferred to the plant in the course of infection by Agrobacterium and integrated in stable manner into the plant genome.

Both Ti-plasmids and Ri-plasmids have two regions that are essential for the production of transformed cells. One of those regions, the transfer-DNA (T-DNA) region, is transferred to the plant and leads to the induction of tumours. The other region, the virulence-imparting (vir) region, is essential only for the formation of the tumours, not for their maintenance. The dimensions of the transfer-DNA region can be enlarged by incorporation of the peptide-encoding DNA sequence without the transferability being impaired. By removing the tumour-inducing genes and incorporating a selectable marker, the modified Ti- or Ri-plasmid can be used as a vector for the transfer of the gene construction according to the invention into a suitable plant cell.

The vir region brings about the transfer of the T-DNA region of Agrobacterium to the genome of the plant cell irrespective of whether the T-DNA region and the vir region are present on the same vector or on different vectors within the same Agrobacterium cell. A vir region on a chromosome also induces the transfer of the T-DNA from a vector into a plant cell.

Thus, for transferring the peptide-encoding DNA into plant cells a system can be used, in which the vir region and the T-DNA region are located on different vectors. Such a system is known as a "binary vector system", and the vector containing the T-DNA is accordingly designated a "binary vector".

Any T-DNA-containing vector that can be transferred into plant cells and permits selection of the transformed cells is suitable for use within the scope of this invention such as, for example, a shuttle vector that comprises the peptide-encoding DNA sequence according to the invention cloned in between the left border sequence (LB) and the right border sequence (RB) and that is capable of stable replication both in *E. coli* and in *A. tumefaciens*.

One of the preferred methods for introducing DNA into a plant cell by means of Agrobacterium is the so-called leaf disk transformation using Agrobacterium (Horsch et al., 1985). Sterile leaf disks from a suitable target plant are incubated with Agrobacterium cells comprising one of the peptide-encoding DNA sequences according to the invention, and are then transferred into or onto a suitable nutrient medium. Especially suitable, and therefore preferred within the scope of this invention, are LS media that have been solidified by the addition of agar and enriched with one or more of the plant growth regulators customarily used.

After incubation for several days, but preferably after incubation for 2 to 3 days at a temperature of from 20° C. to 40° C., preferably from 23° C. to 35° C. and more especially at 25° C. and in diffuse light, the leaf disks are transferred to a suitable medium for the purpose of shoot induction. Especially preferred for the selection of the transformants is an LS medium that does not contain auxin but contains cytokinin instead, and to which a selective substance has been added dependent on the marker gene used. The cultures are kept in the light and are transferred to fresh medium at suitable intervals, but preferably at intervals of one week. Developing green shoots are cut out and cultured further in a medium that induces the shoots to form roots. Especially preferred within the scope of this invention is an LS medium that does not contain auxin or cytokinin but to which a selective substance has been added for the selection of the transformants.

In addition to Agrobacterium-mediated transformation, within the scope of this invention it is possible to use direct transformation methods for the insertion of the gene constructions according to the invention into plant material.

Possible methods for the direct transfer of genetic material into a plant cell comprise, for example, the treatment of protoplasts using procedures that modify the plasma membrane, for example polyethylene glycol treatment, heat shock treatment, sonication or electroporation, or a combination of those procedures (Shillito et al., 1985).

In the electroporation technique, plant protoplasts or cells together with plasmids that comprise the peptide-encoding DNA sequence are subjected to electrical pulses of high field strength. This results in a reversible increase in the permeability of biomembranes and thus allows the insertion of the plasmids. Electroporated plant protoplasts renew their cell wall, divide and form callus tissue. Selection of the transformed plant cells can take place with the aid of the above-described phenotypic markers.

A further method for the direct introduction of genetic material into plant cells, which is based on purely chemical procedures and which enables the transformation to be carried out very efficiently and rapidly, is described in Negrutiu et al. (1987).

Further means for inserting genetic material contained in a vector directly into a plant cell comprise using purely physical procedures, for example by microinjection using finely drawn micropipettes (Neuhaus et al., 1987) or by bombarding the cells with microprojectiles that are coated with the transforming DNA ["Microprojectile Bombardment" (Wang et al., 1988)] or are accelerated through a DNA containing soluting in the direction of the cells to be transformed by a pressure impact thereby being finly atomized into a fog with the solution as a result of the pressure impact (EP 434,616).

Screening of plant cells, tissue and plants for the presence of specific DNA sequences is performed by Southern analysis (Southern, 1975). Details of this procedure are given in Maniatis et al. (1982). This screening can also be performed by the use of Polymerase Chain Reaction procedures (PCR). PCR procedures are described in detail in Mullis et al. (1987) and Erlich (1989).

Transformation of the plant cells includes separating transformed cells from those that have not been transformed. One convenient method for such separation or selection is to incorporate into the material to be inserted into the transformed cell a gene for a selection marker. As a result only those cells that have been successfully transformed will contain the marker gene. The translation product of the marker gene will then confer a phenotypic trait that will make selection possible. Usually the phenotypic trait is the ability to survive in the presence of some chemical agent, such as an antibiotic, e.g., kanamycin, G418, paromomycin, etc., which is placed in a selection media.

Some examples of genes that confer antibiotic resistance include, for example, those coding for neomycin phosphotransferase [kanamycin resistance, Velten et al. (1984)]; hygromycin phosphotransferase [hygromycin resistance, van den Elzen et al. (1985)], the kanamycin resistance (NPT II) gene derived from Tn5 [Bevan et al. (1983); McBride et al. (1990)], the PAT gene described in Thompson et al. (1987), and chloramephenicol acetyltransferase.

An example of a gene useful primarily as a screenable marker in tissue culture for identification of plant cells containing genetically engineered vectors is a gene that encodes an enzyme producing a chromogenic product. One example is the gene coding for production of β-glucuronidase (GUS). This enzyme is widely used and its preparation and use is described in Jefferson (1987).

Once the transformed plant cells have been cultured on the selection media, surviving cells are selected for further study and manipulation. Selection methods and materials are well known to those of skill in the art, allowing one to choose surviving cells with a high degree of predictability that the chosen cells will have been successfully transformed with exogenous DNA.

After transformation of the plant cell or plant using, for example, the Agrobacterium Ti-plasmid, those plant cells or plants transformed by the Ti plasmid so that the enzyme is expressed, can be selected by an appropriate phenotypic marker. These phenotypical markers include, but are not limited to, antibiotic resistance. Other phenotypic markers are known in the art and may be used in this invention.

Positive clones are regenerated following procedures well-known in the art. Subsequently transformed plants are evaluated for the presence of the desired properties and/or the extent to which the desired properties are expressed. A first evaluation may include, for example, the level of bacterial/fungal resistance of the transformed plants, stable heritability of the desired properties, field trials and the like.

Plant pathogens which may be the targets of the present invention include for example members of the following classes: bacteria (for example Corynebacterium, Pseudomonas, Xanthomonas and Erwinia); fungi, such as Fungi imperfecti (for example, Botrytis, Fusarium, Septoria); Ascomycetes (for example, Erysiphe, Monilia); Oomycetes (for example, Peronospora, Phytophthora, Plasmopara, Colletotrichum and Pythium); Basidiomycetes (for example, Rhizoctonia and Puccinia); as well as to insects and nematodes (for example species of Meloidogyne, Caenorhabditis, Globora, Heterodera and Pratylenchus). For example, the fungal pathogens may include the species *Botrytis cinerea; Colletotrichum lagenarium; Erysiphe graminis; Monilia fructicola; Peronospora tabacina; Phytophthora parasitica; Plasmopara viticola; Pythium ultimum; Rhizoctonia solani;* and *Septoria nodorum.*

Target crops to be protected within the scope of the present invention include for example the following species of plants: maize, cereals (e.g., wheat, barley, rye, oats, rice, sorghum and related crops), beet (e.g., sugar beet and fodder beet), drupes, pomes and soft fruit (e.g., apples, pears, plums, peaches, almonds, cherries, strawberries, raspberries and black-berries), leguminous plants (e.g., beans, lentils, peas, soybeans), oil plants (e.g., rape, mustard, poppy, olives, sunflowers, coconuts, caster oil plants, cocoa beans, groundnuts), cucumber plants (e.g., cucumber, marrows, melons), fibre plants (e.g., cotton, flax, hemp, jute), citrus fruit (e.g., oranges, lemons, grapefruit, mandarins), vegetables (e.g., spinach, lettuce, asparagus, cabbages, carrots, onions, tomatoes, potatoes, paprika), Lauraceae (e.g., avocados, cinnamon, camphor), or plants such as tobacco, nuts, coffee, sugar cane, tea, vines, hops, bananas and natural rubber plants, as well as ornamentals.

The present invention further embraces the preparation of anti-pathogenic compositions comprising homogeneously mixing a peptide according to the invention with one or more suitable carriers and/or adjuvants customarily used in agricultural peptide formulations. The active component is homogeneously mixed with one or more compounds or groups of compounds described herein. The present invention also relates to methods of protecting plants from the attack of plant pathogens, which comprise application of the active component, or anti-pathogenic compositions containing the active component, to the plant or to the plant pathogen's habitat.

In one embodiment the peptides of the present invention are applied prophylactically or curatively in the form of compositions together with one or more agriculturally acceptable carriers, and can be applied to the crop area or plant to be treated, simultaneously or in succession, with further compounds. These compounds can be both fertilizers or micro-nutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying active components of the present invention or an agrochemical composition which contains at least one of the active components is leaf application. The number of applications and the rate of application depend on the intensity of infestation by the corresponding pathogen. However, the active components can also penetrate the plant through the roots via the soil (systemic action) by impregnating the locus of the plant with a liquid composition, or by applying the compounds in solid form to the soil, e.g. in granular form (soil application). The active components may also be applied to seeds (coating) by impregnating the seeds either with a liquid formulation containing active components, or coating them with a solid formulation. In special cases, further types of application are also possible, for example, selective treatment of the plant stems or buds.

The active components are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active component (a.i.) per hectare (ha), preferably from 100 g a.i./ha to 2 kg a.i./ha, most preferably from 200 g a.i./ha to 500 g a.i./ha.

The formulations, compositions or preparations containing the active component, and, where appropriate, a solid or liquid adjuvant, are prepared in known manner, for example by homogeneously mixing and/or grinding the active component with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active component to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkine earth metal salts or unsubstituted or substituted ammoniums salts and have a 8 to 22 carbon alkyl radical which also includes the alkyl moiety of alkyl radicals, for example, the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutyl-napthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable nonionic surfactants.

Cationic surfactants are preferably quaternary ammonium salts which have, as N-substituent, at least one $C_8-C_{22}$alkyl radical and, as further substituents, lower unsubstituted or halogenated alkyl, benzyl or lower hydroxyalkyl radicals. The salts are preferably in the form of halides methylsulfates or ethylsulfates, e.g. stearyltrimethylammonium chloride or benzyldi(2-chloroethyl)ethylammonium bromide.

The surfactants customarily employed in the art of formulation are described, for example, in McCutcheon's Detergents and Emulsifiers Annual (1979), and Sisely and Wood (1980).

The agrochemical compositions usually contain from about 0.1% to about 99%, preferably about 0.1% to about 95%, and most preferably from about 3% to about 90% of the active component, from about 1% to about 99.9%, preferably from about 1% to about 99%, and most preferably from about 5% to about 95% of a solid or liquid adjuvant, and from about 0% to about 25%, preferably about 0.1% to about 25%, and most preferably from about 0.1% to about 20% of a surfactant.

Whereas commercial products are preferably formulated as concentrates, the end user will normally employ dilute formulations.

A further object of the present invention is the use of a phospholipid transfer protein as an active ingredient in an antipathogenically effective composition according to the invention.

A further object of the present invention is the use of the peptide according to the invention as an active ingredient in an antipathogenically effective composition according to the invention. Preferred is the use of a peptide containing at its N-terminal end a hydrophobic region which preferably comprises one of the following amino acid sequences:
(a) Ala Ile Thr Cys Gly Gln Val Ser Ser Ala Leu or
(b) Ala Ile Ser Cys Gly Gln Val Ser Ser Ala Leu Ser Pro Cys Ile Ser Tyr Ala Arg Gly Asn Asn Ala
(c) Ala Ile Ser Cys Gly Gln Val Ser Ser Ala Leu Ser Pro Cys Ile Ser Tyr Ala Arg Gly Asn Gly Ala
(d) an N-terminal amino acid sequence that is substantially homologous to at least one of the above sequences,
as an active ingredient in an antipathogenically effective composition according to the invention.

It is a further object of the present invention to provide a method of protecting plants from the attack of plant pathogens, preferably pathogenic bacteria and/or fungi, which comprises applying an anti-pathogenically effective amount of the inventive peptide or composition to the plant or to the plant pathogen's habitat.

It is a further object of the present invention to provide a method of controlling plant pathogens comprising expressing an anti-pathogenically effective amount of a phospholipid transfer protein in a transgenic plant.

It is a further object of the present invention to provide a method of controlling plant pathogens comprising expressing an anti-pathogenically effective amount of the inventive peptide.

It is a further object of the present invention to provide a method of controlling plant pathogens comprising expressing an anti-pathogenically effective amount of an active ingredient; wherein the active ingredient comprises a phospholipotransfer protein and a lytic peptide.

It is a further object of the present invention to provide a method of controlling plant pathogens comprising expressing an anti-pathogenically effective amount of an active ingredient; wherein the active ingredient comprises the inventive peptide.

It is a further object of the present invention to provide a method of controlling plant pathogens comprising the steps of:
a) preparing a transgenic plant comprising recombinant DNA sequences encoding one or more phospholipid transfer protein;
b) causing the transgenic plant to synthesize one or more phospholipid transfer protein.

Also comprised is a method of controlling plant pathogens comprising the steps of:
a) preparing a transgenic plant comprising recombinant DNA sequences encoding one or more peptides as shown in SEQ ID NO: 3 to 5 including peptides that have substantial sequence homology thereto,
b) causing the transgenic plant to synthesize one or more peptides as shown in SEQ ID NO: 3 to 5 including peptides that have substantial sequence homology thereto.

Further comprised is a method of controlling plant pathogens comprising the steps of:
a) preparing a transgenic plant comprising recombinant DNA sequences encoding an anti-pathogenically effective amount of an active ingredient; wherein the active ingredient comprises a peptide as shown in SEQ ID NO: 3 to 5 including peptides that have substantial sequence homology thereto and a lytic peptide,
b) causing the transgenic plant to synthesize an anti-pathogenically effective amount of an active ingredient; wherein the active ingredient comprises a peptide as shown in SEQ ID NO: 3 to 5 including peptides that have substantial sequence homology thereto and a lytic peptide.

The present invention also relates to a method of controlling plant pathogens comprising the steps of:
a) preparing a transgenic plant comprising recombinant DNA sequences encoding one or more phospholipid transfer protein;
b) causing the transgenic plant to synthesize one or more phospholipid transfer protein.

Further comprised is a method of preparing a transgenic plant which is able to synthesize anti-pathogenically effective amounts of an active ingredient compring
a) preparing a transgenic plant comprising recombinant DNA sequences encoding a phospholipidtransfer protein and optionally a lytic peptide; or
b) preparing two or more transgenic plants comprising recombinant DNA sequences encoding a phospholipidtransfer protein and optionally a lytic peptide and crossing said plants using conventional breeding techniques.

It is also an object of the present invention to provide a method of preparing a transgenic plant which is able to synthesize anti-pathogenically effective amounts of an active ingredient comprising
a) preparing a transgenic plant comprising recombinant DNA sequences encoding a peptide as shown in SEQ ID NO: 3 to 5 including peptides that have substantial sequence homology thereto and optionally a lytic peptide; or b) preparing two or more transgenic plants comprising recombinant DNA sequences encoding a peptide as shown in SEQ ID NO: 3 to 5 including peptides that have substantial sequence homology thereto and optionally a lytic peptide and crossing said plants using conventional breeding techniques.

After the general description of the present invention, for the purpose of better understanding reference will now be made to specific Examples which are incorporated into the description for illustrative purposes and are not of a limiting nature unless there is a specific indication to the contrary.

NON-LIMITING WORKING EXAMPLES

Example 1

Growth of barley plants

Barley c.v. Betzes and barley c.v. Bomi is sown in vermiculite in shallow trays [15.×30 cm×8 cm]. The trays are watered with sterile water and kept in the dark in a cabinet for 7 days. The coleoptiles and/or shoots are removed, immediately frozen in liquid nitrogen and stored at −70° C.

Example 2

Protein purification 2.1: Tissue extraction

About 20 g fresh weight of harvested coleoptiles and/or shoots are ground to powder with liquid nitrogen using a mortar and pestle. The ground material is extracted with 4 volumes of a buffer solution (80 ml) comprising 0.1 M Tris-HCl, 10 mM EDTA, pH 7.5.

The combined extract is centrifuged at 5000× g for 10 minutes at 4° C. The supernatant is discarded and the pellet extracted twice with distilled $H_2O$ [80 ml each time].

2.2: Cell wall extraction

Following the extraction with $H_2O$ the pellet is extracted with 50 ml of a high salt solution comprising 1.5 M LiCl made up in $H_2O$. The extraction mixture is kept at 4° C. for 1 hour. The extraction mixture is then centrifuged at 5000× g for 10 minutes at 4° C.

The supernatant is retained and either (a) dialyzed against 5 l of distilled $H_2O$ using a membrane capable of retaining molecules of >3000 kD [Spectra/Por 6; MWCO: 3000; SPECTRUM®, Medical Industries, Inc. L.A. USA];

(b) desalted by passage through a Sephadex G25 [Pharmacia] column; or (c) precipitated with solid ammonium sulfate [43.7 g per 100 ml of supernatant].

If step (a) or (b) above is used the desalted supernatant is concentrated by freeze drying.

2.3 HPLC fractionation

The extract being concentrated as described above [freeze dried or ammonium sulfate precipitate], is redissolved in 1 ml $H_2O$ containing 0.1% [w/v] trifluoroacetic acid [TFA] and then subjected to HPLC fractionation. The chromatography system used consists of a Ultrapore C-4 column [Beckman], a 126System Gold Beckman pump and a Beckman UV 166System Gold detector. UV detection is performed at a wavelength of 214 nm. The above 1 ml fraction is injected into the C-4 column. Initially, the mobile phase is 100% distilled water containing 0.1% [w/v] TFA. The flow rate is set to 0.5 ml/min at room temperature. Subsequently, a linear gradient of 0 to 30% [v/v] isopropanol over 180 min [=90 ml] is applied to the column, followed by a gradient of 30 to 50% [v/v] isopropanol over 15 min [=7.5 ml]. 3 to 10 ml fractions are collected and concentrated to dryness in vacuo in a Savant Speed Vac Concentrator. The fractions eluting after a retention time of about 96.3 min [CW 18], 104.4 min [CW 20], 106.3 min [CW 21] and 111 min [CW 22] are collected and subjected to further analysis. Protein is determined according to the method of Folin and Lowry (Lowry et al., 1951) or using the BCA Protein Assay Reagent (PIERCE, Rockford, Ill., USA). Peaks corresponding to CW18, CW 20, CW 21 and CW22 are collected by hand as single fractions, discarding the initial 20 sec and the last 20 sec of the "uphill" and the "down-hill" portions of the peaks. The resulting protein fractions appear homogenous by three types of electrophoresis (acid, basic and SDS-PAGE) and by N-terminal sequencing.

2.4 Molecular weight

The molecular weight of peptides CW18 and CW21 is 8.78 kD and 8.66 kD, respectively, as determined by mass spectroscopy.

2.5 Amino acid composition

The relative proportion of the amino acids in the amino acid composition of peptides CW18, CW21, CW20 and CW22 is determined using pre-column phenylisothiocyanat derivatization according to Bidlingmeyer et al. (1984) after 24 h total hydrolysis.

The results given in Table 1 are to be understood as % (measured) of each of the designated amino acids with respect to all of the amino acids which gave rise to similar measurement.

TABLE 1

Amino acid composition of peptides CW18, CW21, CW20 and CW22 (residues/100)

| AA | CW18 | CW21 | CW20 | CW22 |
|---|---|---|---|---|
| Cys | 6.2 | 5.6 | 6.5 | 5.5 |
| Asx* | 3.9 | 3.9 | 5.2 | 5.2 |
| Glx* | 5.0 | 5.1 | 4.6 | 5.4 |
| Ser | 11.9 | 12.6 | 11.6 | 11.4 |
| Gly | 13.3 | 12.7 | 13.0 | 13.3 |
| His | 1.3 | — | 1.1 | — |
| Arg | 6.0 | 4.1 | 3.4 | 3.6 |
| Thr | 5.5 | 2.8 | 3.2 | 2.5 |
| Ala | 15.9 | 19.3 | 19.3 | 18.9 |
| Pro | 6.0 | 7.9 | 6.7 | 6.0 |
| Tyr | 3.0 | 2.1 | 2.0 | 2.2 |
| Val | 6.4 | 6.3 | 6.4 | 6.8 |
| Ile | 5.0 | 7.1 | 5.9 | 5.8 |
| Leu | 4.9 | 4.3 | 4.6 | 4.6 |
| Lys | 5.7 | 6.2 | 6.4 | 7.7 |

Asx means either Asn or Asp
Gk means either Gln or Glu 2.6 Amino acid sequences

To identify the N-terminal amino acid sequence and the complete amino acid sequence, respectively, of the inventive peptides automated Edman degradations are performed with an Applied Biosystems 470A gas-phase sequenzer [Applied Biosystems Inc., Foster City, Calif., USA]. PTH amino acids are identified using an Applied Biosystems 120A PTH analyzer.

The amino acid sequence for peptide CW21 is SEQ ID NO:4. The amino acid sequence for peptide CW18 is SEQ ID NO:3 (Bomi) and SEQ ID NO:5 (Betzes), respectively. The N-terminal amino acid sequences (12 amino acids) of CW20 and CW22 are identical to the N-terminal sequence of CW21.

Example 3

Formulations of anti-pathogenically effective liquid compositions

In the following, percentages of compositions are given by weight.

| Solutions: | a | b | c | d |
|---|---|---|---|---|
| Peptide | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160° C. to 190° C.) | — | — | 94% | — |

These solutions are suitable for application in the form of microdrops.

Example 4

Antibacterial assay (a) Microtiter plates are selected to investigate the inhibitory effect of CW18 and CW21 peptides. The test substances [5 $\mu$g] are dissolved in water and added to ⅓ concentrated N-1 medium [pH 7.2 to 7.4: Difco Beef Extract 1.0 g; Difco Yeast Extract 2.0 g; Difco Bactopeptone 5.0 g; NaCl 5.0 g; add $H_2O$ to 1000 ml] which has been previously inoculated with bacteria of the strain *C. sepedonicum* in a concentration of about $10^4$ bacteria/ml to give a final volume of 150 $\mu$l. The final concentrations of the test substances in the media range from $10^{-8}$ M to $10^{-5}$ M (assuming an apparent molecular weight of approximately 5 kD).

The growth of the bacteria is evaluated after 48 hours incubation at 25° C. by measuring the absorbance of the medium at 492 nm.

For control purposes two standards are used in the above test that is α1/β thionin from wheat endosperm and LT26-thionin from barley leaves.

Soluble leaf thionins are prepared as described by Reimann-Phillipp et al. (1989) and further purified following the RP-HPLC programm described above for CW18 and CW21. The homogenous LT26 is sequenced up to residue no. 28 and found to be identical to the sequence deduced from cDNA clone DG3 (Bohlmann and Apel, 1987).

Endosperm thionins are obtained by precipitation from petroleum-ether extract as described by Garcia-Olmedo et al. (1968) and further purified by RP-HPLC as described above.

The result of the antibacterial assay is given in FIG. 1.

(b) CW18, CW21, CW20 and CW22 are dissolved in water as required. *C. sepedonicum* (syn. *Clavibacter michiganensis* subsp. sepedonicus) and *Pseudomonas solanacearum* are each inoculated at a final concentration of $10^4$ cfu/ml in sterile microtiter plates at final volumes of 150 $\mu$l (100 $\mu$l peptide+50 $\mu$l nutrient broth, Oxoid). After 16 to 24 hours of incubation at 28° C. growth is recorded by measuring absorbance at 492 nm in an ELISA plate reader.

TABLE 2

Activity of CW18, CW21, CW20, CW22 and thionin against *C. sepedonicum* and *P. solanacearum* (EC-50 inhibition⁺)

| | *C. sepedonicum* | | *P. solanacearum* | |
|---|---|---|---|---|
| Protein | ppm | $\mu$M* | ppm | $\mu$M* |
| barley | | | | |
| CW18 | 1 | 0.1 | 3 | 0.3 |
| CW21 | 3 | 0.3 | 5 | 0.6 |
| CW20 | 1.5 | 0.2 | | |
| CW22 | <1 | <0.1 | 3 | 0.3 |
| Thionin | 5 | 1 | 5 | 1 |

⁺EC-50: amount of peptide required to inhibit by 50% the growth of the bacteria compared to the control
*a mol. wt. of 9,000 is assumed (c) The bacteria are cultured in microtiter plates. The peptides are added to the growth media. Growth as an increase in optical density is measured 2 and 3 days after inoculation. The start inoculum is of $10^5$ bacteria/ml. The concentration of the peptides is 100 ppm.

TABLE 3

Inhibition of the growth of *Xanthomonas oryzae* (% of control)

| | CW18 | CW20 | CW21 | CW22 | Control |
|---|---|---|---|---|---|
| 2 days | 73 | 27 | 40 | 39 | 100 |
| 3 days | 77 | 33 | 29 | 39 | 100 |

Example 5

Antifungal assay (a) The antifungal assay can be performed in analogy to the antibacterial assay described above. Instead of the N1 medium a pea medium is used that has been previously inoculated with about $10^4$ to $10^6$ spores of the fungi to be tested. The final concentrations of the test substances in the media range from 2000 or 200 to 0.2 ppm according to the test organism. The plates are evaluated after incubation in a wet chamber at 23° C. on a shaker in the dark for 48 hours. The different test solutions are tested in duplicate/triplicate samples.

The growth of the pathogen is recorded by measuring the absorbance of the medium at 595 nm.

Compared with untreated controls CW18 and CW21 exhibit strong antifungal activity against several fungal pathogens.

(b) Spores are collected from 8 day old cultures grown at 25° C. on potato dextrose agar (Difco) plates. The spores are harvested according to Broekaert et al. (1990) and stored in 20% glycerol at −20° C. In the growth inhibition assay fungal spore suspensions (10,000 spores/ml) are grown at 25° C. in 67.5 $\mu$l potato dextrose broth per microtiter well and incubated with proteins dissolved in water as required (total volume 75 $\mu$l). Measurement of culture absorbances at 540 nm correlate linearly with fungal biomass within a broad OD range. After 26 to 44 hours of incubation at 25° C. growth is recorded by measuring absorbance at 540 nm in an ELISA microplate reader. The results presented in tables 4 and 5 belong together.

TABLE 4

Activity of CW18, CW21, CW20, CW22 and thionin against *Fusarium solani* EC-50 values[+]

| Protein | F. solani | |
|---|---|---|
| | ppm | $\mu M$* |
| CW18 | 45 | 5 |
| CW21 | 30 | 3 |
| CW20 | 200 | 20 |
| CW22 | 100 | 10 |
| Thionin | 10 | 2 |

[+]EC-50: amount of peptide required to inhibit by 50% the growth of the fungi compared to the control
*a mol. wt. of 9,000 is assumed

TABLE 5

Activity of a composition containing CW21 and thionin against *Fusarium solani* EC-50[+] values)

| Protein | ppm | $\mu M$* |
|---|---|---|
| 10 ppm CW21 + thionin | 4 | 0.75 |
| 20 ppm CW21 + thionin | 1 | 0.2 |

[+]EC-50: amount of peptide required to inhibit by 50% the growth of the fungi compared to the control
*a mol. wt. of 9,000 is assumed

Example 6
Transformation of Agrobacterium

Binary vectors are transformed into *A. tumefaciens* strain LB4404 by the following method. The Agrobacterium strain is grown at 30° C. overnight in 5 ml of LBMG medium (50% L broth, 50% mannitol-glutamate broth (Garfinkel and Nester, 1980). The 5 ml culture is added to 250 ml of LBMG and shaken vigorously until the culture density reaches an OD=0.6 at 600 nm wavelength. The cells are then collected by centrifugation at 8000× g and resuspended in 5 ml of LBMG. 200 $\mu$l of cells are added to 0.2 to 1 $\mu$g of binary plasmid DNA in LBMG and the mix is frozen immediately in a dry ice/ethanol bath. After 5 minutes the tube is placed in a 37° C. water bath for 5 minutes and then 2 ml of LBMG is added. The suspension is kept in a 30° C. water bath for 2 to 3 hours and then the cells are collected by centrifugation. The cells are resuspended in a minimal volume of LBMG and then plated on selective media (LBMG plates with 100 $\mu$g/ml gentamycin). Colonies appear after 2 to 3 days at 30° C.

Positive colonies are selected and verified by Southern blot analysis and used for plant transformation experiments.

Example 7
Stable Transformation and Regeneration of Transgenic Plants

Plant tissue is transformed with the vectors described above by any technique known in the are Such methods used for transfer of DNA into plant cells include, for example, the direct infection of or co-cultivation of plants, plant tissue or cells with *A. tumefaciens* (Horsch et al., 1985; Marton, 1984), treatment of protoplasts with exogenous DNA by methods such as those described in Paszkowski et al. (1984); EP 164 575; Shillito et al. (1985); Potrykus et al. (1985); Lörz et al. (1985); Fromm et al. (1987); GB 2,140,822; and Negrutiu et al. (1987); incubation with polyethylene glycol (PEG) (Negrutiu et al., 1987); micro-injection [Reich et al. (1986a and b)]; microprojectile bombardment (Klein et al., 1987).

A. Leaf Disk Transformation of Tobacco

Agrobacterium are grown 18 to 24 hours in glutamate salts media adjusted to pH 5.6 and supplemented with 0.15% mannitol, 50 $\mu$g/ml kanamycin, 50 $\mu$g/ml spectinomycin and 1 mg/ml streptomycin before they are diluted to an OD600 of 0.2 in the same media without the antibiotics. The bacteria are then grown for three to five hours before dilution to an OD600 of 0.2 to 0.4 for inoculation of discs of 5 to 7 mm punched from leaves of *Nicotiana tabacum* cv. *xanthi* that have been grown aseptically in GA7 containers, following a modification of the method of Horsch et al. (1985).

The leaf disks are maintained on 0.7% agar containing Murashige and Skoogs major and minor salts (MS), 1 mg/l benzyladenine and 1 mg/ml α-naphthaleneacetic acid for two days before transfer to the same media containing 50 $\mu$g/ml kanamycin, 100 $\mu$g/ml carbenicillin and 100 $\mu$g/ml mefoxin. Shoots which form on the discs are excised and propagated until six plantlets are obtained by subculturing the shoot tips on MS media containing 50 $\mu$g/ml kanamycin in GA7 containers.

The plantlets are rooted on medium containing no hormones and 50 $\mu$g/ml kanamycin, transferred to soil and hardened in a phytotron before transfer to the greenhouse for induction treatment with chemical regulators. At flowering time flowers are induced to selfpollinate. Seeds are harvested following maturation.

B. Production of Transgenic Tobacco Callus and Plants

Agrobacterium is used to transform callus forming from the leaf disks (A). Callus forming on kanamycin-containing MSBN selection medium is maintained on a callus growth medium comprised of MS major, minor salts and Fe-EDTA (Gibco # 500-1117; 4.3 g/l), MS vitamins, 100 mg/l myo-inositol, 20 g/l sucrose, 2 mg/l naphthaleneacetic acid and 0.3 mg/l kinetin.

The callus can be used to regenerate transgenic plants by transferring callus pieces to MSBN medium and following methods described in A.

C. Transformation of Carrot

Agrobacterium are grown as described in A. The bacteria, diluted to an OD600 of 0.2 to 0.4, are then used for inoculation of discs cut from surface sterilized carrots.

To surface sterilize the carrots they are peeled and then soaked 20 minutes in a 10% solution of chlorox. The carrots are rinsed with sterile water, sliced into 5 mm pieces and placed basal side up onto water agar. 20 to 50 $\mu$l of bacteria are then applied to the upper surface of the discs.

D. Transformation of Sunflower

Agrobacterium are grown as described in A. The bacteria, diluted to an OD600 of 0.2 to 0.4, are then used for inoculation of stems of sunflower plants prepared as follows:

Sunflower seeds are soaked 10 min in 10% captan followed by 10 min in 10% chlorox and rinsing with sterile water. The seed coats are removed and the seeds are germinated on 0.7% water agar in the dark for three days, after which they are placed into a labline incubator set at 23° C. with a 12 hour day and night The seedlings are grown for one week before decapitation and inoculation of the bacteria onto the cut stem surface.

E. Transformation of Tomato

Agrobacterium are grown as described in A. The bacteria, diluted to an OD600 of 0.2 to 0.4, are then used for inoculation of stems of tomato seedlings prepared as follows:

Tomato seeds are soaked 20 min in 10% chlorox and rinsed with sterile water. The seeds are germinated on 0.7% water agar in the dark for three days, after which they are placed into a labline incubator set at 23° C. with a 12 hour day and night. The seedlings are grown for one week before decapitation and inoculation of the bacteria onto the cut stem surface.

F. Transformation of Cotton

Agrobacterium are grown as described in A. The bacteria, diluted to an OD600 of 0.2 to 0.4, are then used for inoculation of cotton cotyledons prepared as follows:

The cotton seeds are soaked 20 min in 10% chlorox and rinsed with sterile water. The seeds are germinated on 0.7% water agar in the dark. The seedlings are grown for one week before inoculation of the bacteria onto the cotyledon surface.

G. Preparation of a Special Type of Callus of Zea mays, Elite Inbred line Funk 2717

Zea mays plants of the inbred line Funk 2717 are grown to flowering in the greenhouse, and self pollinated. Immature ears containing embryos approximately 2 to 2.5 mm in length are removed from the plants and sterilized in 10% Clorox solution for 20 minutes. Embryos are aseptically removed from the kernels and plated with the embryo axis downwards on OMS medium containing 0.1 mg/l 2,4-D, 6% (w/v) sucrose and 25 mM L-proline solidified with 0.24% (w/v) Gehrite® (initiation medium). After two weeks' culture in the dark at 27° C., the callus developing on the scutellum is removed from the embryo and plated on B5 medium, (Gamborg et al., 1968), containing 0.5 mg/l 2,4D and solidified with 0.24% (w/v) Gelrite®. The callus is subcultured every two weeks to fresh medium. After a total of eight weeks after placing the embryos on the initiation medium, the special type of callus is identified by its characteristic morphology. This callus is subcultured further on the same medium. After a further period of two months, the callus is transferred to, and serially subcultured on, N6 medium containing 2 mg/l 2,4-D and solidified with Gehrite®.

H. Preparation of a Suspension Culture of Zea mays, Elite Inbred Funk 2717

The callus described in G is subcultured for a total of at least six months. The type of callus chosen for subculture is relatively non-mucilaginous, granular and very friable, such that it separated into small individual cell aggregates upon placing into liquid medium. Cultures containing aggregates with large, expanded cells are not retained. Approximately 500 mg aliquots of the special callus of Zea mays elite inbred funk 2717 are placed into 30 ml of N6 medium containing 2 mg/l 2,4D in 125 ml Delong flasks. After one week of culture at 26° C. in the dark on a gyratory shaker (130 rpm, 2.5 cm throw), the medium is replaced with fresh medium. The suspensions are again subcultured in this way after another week. At that time, the cultures are inspected, and those which do not show large numbers of expanded cells are retained Suspension cultures containing aggregates with large, expanded cells are discarded The preferred tissue consists of densely cytoplasmic dividing cell aggregates which has a characteristically smoother surface than the usual type of cell aggregates. The cultures retained have at least 50% of the cells represented in these small aggregates. This is the desired morphology. These suspensions also have a rapid growth rate, with a doubling time of less than one week. The suspension cultures are subcultured weekly by transferring 0.5 ml PCV (packed cell volume: settled cell volume in a pipette) into 25 ml of fresh medium. After four to six weeks of subculture in this fashion, the cultures increase two- to three-fold per weekly subculture. Cultures in which more than 75% of the cells are of the desired morphology are retained for further subculture. The lines are maintained by always choosing for subculture the flask whose contents exhibit the best morphology. Periodic filtration through 630 $\mu$m pore size stainless steel sieves every two weeks is used in some cases to increase the dispersion of the cultures, but is not necessary.

I. Preparation of Protoplasts from Suspension Cultures of Zea mays 1 to 1.5 ml PCV of the suspension culture cells prepared as in H are incubated in 10 to 15 ml of a filter-sterilized mixture consisting of 4% (w/v) cellulase RS with 1% (w/v) Rhozyme in KMC (8.65 g/l KCl, 16.47 g/l MgCl$_2$.6 H$_2$O and 12.5 g/l CaCl$_2$.H$_2$O, 5 g/l MES, pH 5.6) salt solution. Digestion is carried out at 30° C. on a slow rocking table for a period of 3 to 4 hours. The preparation is monitored under an inverted microscope for protoplast release. The protoplasts which are released are collected as follows: The preparation is filtered through a 100 $\mu$m mesh sieve, followed by a 50 $\mu$m mesh sieve. The protoplasts are washed through the sieves with a volume of KMC salt solution equal to the original volume of enzyme solution. 10 ml of the protoplast preparation is placed in each of several disposable plastic centrifuge tubes, and 1.5 to 2 ml of 0.6 M sucrose solution (buffered to pH 5.6 with 0.1% (w/v) morpholinoethane sulfonic acid (MES and KOH)) layered underneath. The tube is centrifuged at 60 to 100× g for 10 minutes, and the protoplasts banding at the interface collected using a pipette and placed in a fresh tube. The protoplast preparation is resuspended in 10 ml of fresh KMC salt solution, and centrifuged for five minutes at 60 to 100× g. The supernatant is removed and discarded, and the protoplasts resuspended gently in the drop remaining, and then 10 ml of a $^{13}/_{14}$ strength KMC solution gradually added. After centrifuging again for five minutes, the supernatant is again removed and the protoplasts resuspended in a $^{6}/_{7}$ strength KMC solution. An aliquot is taken for counting, and the protoplasts again sedimented by centrifugation. The protoplasts are resuspended at $10^7$ per ml in KM-8p medium or in 0.5 M mannitol containing 6 mM MgCl$_2$ or other suitable medium for use in transformation.

J. Transformation of Zea mays Protoplasts by Electroporation a. All steps except the heat shock are carried out at room temperature (22 to 28° C.). The protoplasts are resuspended in the last step of I in 0.5 M mannitol containing 0.1% (w/v) MES and 6 mM MgCl$_2$. The resistance of this suspension is measured in the chamber of a Dialog Electroporator (DIALOG GmbH, D-400 Düsseldorf 13, Germany) and adjusted to 1 to 1.2 k$\Omega$ using a 300 mM MgCl$_2$ solution. The protoplasts are heat-shocked by immersing the tube containing the sample in a water bath at 45° C. for five minutes, followed by cooling to room temperature on ice. 4 g of linearized plasmid containing a plant-selectable hygromycin resistance gene such as described by Rothstein et al. (1987), or chimeric gene constructs and 20 $\mu$g of calf thymus carrier DNA are added to aliquots of 0.25 ml of this suspension. 0.125 ml of a 24% (w/v) PEG solution (MW 8000) in 0.5 M mannitol containing 30 mM MgCl$_2$ are added to the protoplasts. The mixture is mixed well but gently, and incubated for 10 minutes. The sample is transferred to the chamber of the electroporator and samples pulsed three times at 10 second intervals, at initial voltages of 1500, 1800, 2300 or 2800 Vcm$^{-1}$, and an exponential decay time of 1 $\mu$sec.

The protoplasts are cultured as follows. The samples are plated in 6 cm petri dishes at room temperature. After a further 5 to 15 minutes, 3 ml of KM-8p medium containing 1.2% (w/v) SeaPlaque agarose and 1 mg/l 2,4D are added. The agarose and protoplasts are mixed well and the medium is allowed to gel.

b. a is repeated with one or more of the following modifications:
(1) The resistance of the protoplast preparation is adjusted to 0.5 to 0.7 kΩ.
(2) The PEG used is PEG with a molecular weight of 4000.
(3) No PEG is added, or one-half volume of 12% (w/v) PEG is added.
(4) The pulses are applied at intervals of three seconds.
(5) The protoplasts are plated after the electroporation in dishes placed on a plate cooled to a temperature of 16° C.
(6) The protoplasts are placed in tubes after the electroporation step, washed with 10 ml of 6/7 strength KMC solution or with W5 solution (comprised of 380 mg/l KCl, 18.375 g/l $CaCl_2.2H_2O$, 9 g/l NaCl; 9 g/l glucose, pH 6.0), then collected by centrifugation at 60× g for 10 minutes, resuspended in 0.3 ml of KM medium, and plated as in a
(7) The calf thymus carrier DNA is not added.

K. Transformation of *Zea mays* Protoplasts by Treatment with PEG a. The protoplasts are resuspended at the last step of I in a 0.5 M mannitol solution containing 12 to 30 mM $MgCl_2$. A heat shock of 45° C. for five minutes is given as described in J. The protoplasts are distributed in aliquots for transformation in centrifuge tubes, 0.3 ml of suspended protoplasts per tube. During the next 10 minutes the following are added: DNA (as for J) and PEG solution (MW 6000, 40% (w/v); containing 0.1 M $Ca(NO_3)_2$ and 0.4 M mannitol; pH 8 to 9 with KOH) to give a final concentration of 20% PEG. The aliquots are incubated for 30 minutes with occasional gentle shaking, and then the protoplasts are placed in petri dishes (0.3 ml original protoplast suspension per 6 cm diameter dish) and cultured as described in J.

b. a is repeated and the protoplasts are washed after 30 minutes of incubation in the PEG solution of a by adding 0.3 ml of W5 solution five times at two- to three-minute intervals. The protoplast suspension is centrifuged, the supernatant removed, and the protoplasts are cultured as for Example J.a c. a and b are repeated with the modification that the final concentration of PEG is between 13 and 25% (w/v).

L. Regeneration of Callus From Protoplasts

The plates containing the protoplasts in agarose are placed in the dark at 26° C. After 14 days, colonies arise from the protoplasts. The agarose containing the colonies is transferred to the surface of a 9 cm diameter petri dish containing 30 ml of N6 medium containing 2 mg/l 2,4D, solidified with 0.24% w/v Gelrite®. This medium is referred to as 2N6. The callus is cultured further in the dark at 26° C. and callus pieces subcultured every two weeks onto fresh solid 2N6 medium.

M. Selection of Transformed Callus of *Zea mays*

L is repeated with the modification that 100 mg/l or 200 mg/l hygromycin B is added to the 2N6 medium in order to select for transformed cells.

N. Regeneration of Corn Plants a. Callus is placed on 2N6 medium for maintenance and on ON6 (comprising N6 medium lacking 2,4D) and N61 medium (comprising N6 medium containing 0.25 mg/l 2,4D and 10 mg/l kinetin) to initiate regeneration. Callus growing on ON6 and N61 media is grown in the light (16 hours/day light of 840 to 8400 lx from white fluorescent lamps). Callus growing on N61 medium is transferred to ON6 medium after two weeks, as prolonged time on N61 medium is detrimental. The callus is subcultured every two weeks even if the callus is to be transferred again on the same medium formulation. Plantlets appear in about four to eight weeks. Once the plantlets are at least 2 cm tall, they are transferred to ON6 medium in GA7 containers. Roots form in two to four weeks, and when the roots look well-formed enough to support growth, the plantlets are transferred to soil in peat pots, under a light shading for the first four to seven days. It is often helpful to invert a clear plastic cup over the transplants for two to three days to assist hardening off. Once the plants are established, they are treated as normal corn plants and grown to maturity in the greenhouse. In order to obtain progeny plants are self pollinated or crossed with wild type.

b. a is repeated with the modification that 100 mg/l or 200 mg/l hygromycin B is added to the medium used to maintain the callus.

Example 8
Development of transgenic T3 seed lines

Genotype designations for transgenic plants are used herein according to the following convention: the initial plant resulting from a transformation event and having grown from tissue culture is designated a Ti plant. Plants resulting from self pollination of the natural flowers of the T1 plant, are designated T2, having acquired a new genotype during the normal meiotic process. Likewise, seeds borne from self-pollination of the natural flowers of T2 plants (i.e. grown from T2 seed) are designated T3, etc.

Transgenic plants (T1) are grown to maturity. Flowers are allowed to self-pollinate and seed pods are collected after normal dessication. Seeds from each individual plant are collected and stored separately. Each seed lot is tested by genetic segregation analysis to determine the number of Mendelian loci bearing the kanamycin resistance trait. 12 seeds are surface-sterilized by multiple washing in 2% hypochlorite containing 0.02% (v/v) Tween-20, followed by rinses in sterile water. Approximately 150 of the seeds are placed on filter paper saturated with 0.2× MS salts (Murashige and Skoog, 1962) containing 150 μg/ml kanamycin. Following germination and expansion of the cotyledons to approximately 5 mm, the ratio of normal-green (kan-r) versus bleached (kan-s) cotyledons is determined. Only those 72 seed lots exhibiting an approximately 3:1 (kan-r:kan-s) ratio are kept for further analysis; this segregation ratio is indicative of a single Mendelian locus bearing the kanamycin marker gene.

Four to ten plants are grown to maturity from each T2 seed lot (using the same conditions described above), and are allowed to self-pollinate. T3 seed collection, seed sterilization, and seed germination are as described above for the T2 seed. T3 seed lots in which 100% of the tested seeds (n=150) exhibit the kan-r phenotype are assumed to be homozygous for the trait (i.e. resulting from a homozygous T2 parent plant) and are kept for phenotypic analysis.

Conventional breeding techniques are then used to get all genes into the same plant.

BIBLIOGRAPHY

Benzon, J. R., Hare, P. E., Proc. Natl. Acad. Sci. USA 72:619–622 (1975)
Bernhard, W. R., Somerville, C. R., Arch. Biochem. Biophys. 269:695–697 (1989)
Bernhard, W. R., Thoma, S., Botella, J., Somerville, C. R., Plant Physiol. 95:164–170 (1991)
Bevan, M. W., Flavell, R. B., Chilton, M. -D., Nature 304:184–187 (1983)
Bidlingmeyer, B. A., Cohen, S. A., Tarvin, T. L., J. Chrom. 336:93–104 (1984)
Bohlmann, H., Apel, K., Mol. Gen. Genet. 207:446–454 (1987)

Bouillon, P., Drischel, C., Vergnolle, C., Duranton, H., Kader, J -C., Eur. J. Biochem. 166:387–391 (1987)

Broekaert, W. F., Terras, F. R. G., Cammue, B. P. A., Vanderleyden, J., FEMS Microbiol. Lett. 69:55–60 (1990)

Campos, F. A. P., Richardson, M., FEBS Lett. 167:221–225 (1984)

Christou, P., McCabe, D. E., Swain, W. F., Plant Physiol. 87:671–674 (1988)

Crossway, A., Hauptli, H., Houck, C. M., Irvine, J. N, Oakes, J. V., Perani, L. A., BioTechniques 4:320–334 (1986)

Datta, S. K., Peterhans, A., Datta, K., Potrykus, I., Bio/Technology 8:736–740 (1990)

van den Elzen, P. J. M., Townsend, J., Lee, K. Y., Bedbrook, J. R., Plant. Mol. Biol. 5:299–392 (1985)

Erlich, H. A. (Hrsg.), PCR Technology, Stockton Press, New York (1989)

Fromm, M., Callis, J., Taylor, L. P., Walbot, V., Methods in Enzymology 153:351–366 (1987)

Fromm, M. E., Morrish, F., Armstrong, C., Williams, R. Thomas, J., Klein, T. M., Bio/Technology 8:833–839 (1990)

Garcia-Olmedo, F., Sotelo, I., Garcia-Faure, R., Anales Inst. Nac. Invest. Agro. 17:433–443 (1968)

Gordon-Kamm, W. J., Spencer, T. M., Mangano, M. L., Adams, T. R., Daines, R. J., Start, W. G., O'Brien, J. V., Chambers, S. A., Adams, W. R., Willetts, N. G., Rice, T. B., Mackey, C. J., Krueger, R. W., Kausch, A. P., Lemaux, P. G., The Plant Cell 2:603–618 (1990)

Hinchee, M. A. W., Connor-Ward, D. V., Newell, C. A., McDonnell, R. E., Sato, S. J., Gasser, C. S., Fischhoff, D. A., Re, D. B., Fraley, R. T., Horsch, R. B., Biotechnology 6:915–922 (1988)

Hohn, T., Richards, K., Lebeurier, G., in: Gene cloning in organisms other than *E. coli,* Current Topics in Microbiology and Immunology 96:193–220 (1982)

Horsch, R. B., Fry, J. E., Hoffmann, N. L., Eichholtz, D., Rogers, S. G., Fraley, R. T., Science 227:1229–1231 (1985)

Jefferson, R. A., Plant Molecular Biology Reporter 5:387–405 (1987)

Joersbo, M., Brunstedt, J., Plant Cell Reports 9:207–210 (1990)

Kaeppler, H. F., Gu, W., Somers, D. A., Rines, H. W., Cockburn, A. F., Plant Cell Reports 9:415–418 (1990)

Klein, T. M., Fromm, M., Weissinger, A., Tomes, D., Schaaf, S., Sletten, M., Sanford, J. C., Proc. Natl. Acad. Sci. USA 85:4305–4309 (1988)

Klein, T. M., Gradziel, T., Fromm, M. E., Sanford, J. C., Biotechnology 6:559–563 (1988)

Klein, T. M., Kornstein, L., Sanford, J. C, Fromm, M. E., Plant Physiol. 91:440–444(1989)

Klein, T. M., Wolf, E. D., Wu, R., Sanford, J. C., Nature 327:70–73 (1987)

Lathe, R., J. Mol. Biol. 183:1–12 (1985)

Lehrer, R. I., Szklarek, D., Ganz, T., Selsted, M. E., Infection and Immunity 52:902–904 (1986)

Lörz, H., Baker, B., Schell, J., Mol. Gen. Genet. 199:178–182 (1985)

Lowry, O. H. Rosebrough, N. J., Farr, A. L., Randall, R. J., J. Biol. Chem. 193:265–275 (1951)

Maniatis, T., Fritsch, E. F., Sambrook, J., Molecular cloning, a laboratory manual, Cold Spring Harbor Laboratory, Cold Spring Harbor (1982)

Marton, L., in: Cell Culture and Somatic Cell Genetics of Plants 1:514–521 (1984)

Mauch, F., Mauch-Mani, B., Boller, T., Plant Phys. 88:936–942 (1988)

McBride, K. E., Summerfelt, K. R., Plant Mol. Biol. 14:269–276 (1990)

McCabe, D. E., Swain, W. F., Martinell, B. J., Christou, P., Biotechnology 6:923–926 (1988)

McCutcheon's Detergents and Emulsifiers Annual, MC Publishing Corp., Ringwood, N.J. (1979)

Molina, P., Arencibia, A., Gutiérrez, C., Fuentes, A., Menéndez, E., Grenidge, V., de la Riva, G., Selman-Houssein, G., Advances in Gene Technology: Feeding the World in the 21st Century 60, Miami Winter Symposium (1992)

Morelli, G., Nagy, F., Fraley, R. T., Rogers, S. G., Chua, N. H., Nature 315:200–204 (1985)

Mullis, K. B., Faloona, F. A., Meth. Enzymol. 155:335–350 (1987)

Mundy, J., Rogers, J. C., Planta 169:51–63 (1986)

Murashige, T., Skoog, F., Physiol. Plant. 15:473–497 (1962)

Negrutiu, I., Shillito, R., Potrykus, I., Biasini, G., Sala, F., Plant Mol. Biol. 8:363–373 (1987)

Neuhaus et al., Theor. Appl. Genet. 75:30–36 (1987)

Paszkowski, J., Shillito, R. D., Saul, M., Mandak, V., Hohn, T., Hohn, B., Potrykus, I., EMBO J. 3:2717–2722 (1984)

Petit et al., Mol. Gen. Genets 202:388 (1986)

Pierce, D. A., Mettler, L. J., Lachmansigh, A. R., Pomeroy, L. M., Weck, E. A., Mascarenhas, D., Plant Gene Systems and their Biology, 301–310, Alan R. Liss, Inc. (1987)

Potrykus, I., Paszkowski, J., Saul, M. W., Petruska, J., Shillito, R. D., Mol. Gen. Genet. 199:169–177 (1985)

Reich, T. J., Iyer, V. N., Haffner, M., Holbrook, L. A., Miki, B. L., Can. J. Bot. 64:1259–1267 (1986)

Reich, T. J., Iyer, V. N., Mild, B. L., Biotechnology 4:1001–1004 (1986)

Reimann-Phillipp, U., Behnke, S., Batschauer, A., Schafer, E., Apel, K., Eur. J. Biochem. 182:283–289 (1989)

Reimann-Philipp, U., Schrader, G., Martinoia, E., Barkholt, V., Apel, K., J. Biol. Chem. 264:8978–8984 (1989)

Riggs, C. D., Bates, G. W., Proc. Nat. Acad. Sci. USA 83:5602–5606 (1986) Sanford, J. C., Klein, T. M., Wolf, E. D., Allen, N., Particulate Science and Technology 5:27–37 (1987)

Schlumbaum, A., Mauch, F., Vögeli, U., Boller, T., Nature 324:365–367 (1986)

Shillito, R. D., Saul, M. W., Paszkowski, J., Müller, M., Potrykus, I., Biotechnology 3:1099–1103 (1985)

Sisely and Wood, Encyclopedia of Surface Active Agents, Chemical Publishing Co., New York, (1980)

Sossountzov, L., Ruiz-Avila, L., Vignols, F., Jolliot, A., Arondel, V., Tchang, F., Grosbois, M., Guerbette, F., Migniac, E., Delseny, M., Puigdomenèch, P., Kader, J -C., Plant Cell 3:923–933 (1991)

Sterk, P., Booij, H., Schellekens, G. A., van Kammen, A., de Vries, S. C., Plant Cell 3:907–921 (1991)

Southern, E. M., J. Mol. Biol. 98:503–517 (1975)

Svensson, B., et al., Carlsberg Res Commun 51:493–500 (1986)

Takishima, K., Watanabe, S., Yamada, M., Mamiya, G., Biochim. Biophys Acta 870:248–255 (1986)

Tchang, F., This, P., Stiefel, V., Arondel, V., Morch, M -D., Pages, M., Puigdomenech, P., Grellet, F., Delseny. M., Bouillon, P., Huet, J -C., Guerbette, F., Beauvais-Cante, F., Duranton, H., Pernollet, J -C., Kader, J -C., J. Biol. Chem. 263:16849–16855 (1988)

Thompson, C. J., Movva R. N., Tizard, R., Crameri, R., Davies, J. E., Lauwereys, M. Botterman, J., EMBO J. 6:2519–2523 (1987)

Torres-Schumann, S., Godoy, J. A., Pintor-Toro, J. A., Plant Mol. Biol. 18:749–757 (1992)

Velten, J., Velten, L., Hain, R., Schell, J., EMBO J. 3:2723–2730 (1984)
Yamnada, M., Plant Cell Physiol. 33:1–6 (1992)
Wang, Y -C., et al., Plant Mol. Biol. 11:433–439 (1988)
Weising, K., Schell, J., Kahl, G., Annual Rev. Genet. 22:421–477 (1988)

EP 164,575
EP 434,616
EP 462,065
WO 89/04371
U.S. Pat. No. 4,945,050
GB 2,140,822

What is claimed is:

1. An isolated DNA comprising a sequence encoding amino acids according to SEQ. ID No. 1, 2, 3, 4, 5, or 6.

2. A recombinant DNA comprising a peptide-encoding sequence wherein the peptide-encoding sequence encodes a peptide according to SEQ ID No. 1, 2, 3, 4, 5, or 6.

3. A vector comprising the isolated DNA sequence according to claim 1.

4. A vector comprising the recombinant DNA sequence according to claim 2.

5. A transgenic plant expressing a recombinant DNA of claim 2.

6. A transgenic plant comprising a vector according to claim 3.

7. A method of preparing a transgenic plant comprising:
   a) preparing a transgenic plant comprising recombinant DNA of claim 2 and optionally a lytic peptide; or
   b) preparing two or more transgenic plants comprising recombinant DNA of claim 2 and optionally a lytic peptide and crossing said plants using conventional breeding techniques.

8. A method of preparing a transgenic plant which is able to synthesize anti-pathogenically effective amounts of an active ingredient comprising a peptide having an amino acid sequence comprising SEQ ID NO. 3, 4 or 5, wherein the method comprises:
   a) preparing a transgenic plant comprising recombinant DNA sequences encoding said peptide and optionally a lytic peptide; or
   b) preparing two or more transgenic plants comprising recombinant DNA sequences encoding said peptide and optionally a lytic peptide and crossing said plants using conventional breeding techniques.

9. An isolated DNA comprising a sequence encoding 11 consecutive amino acids set forth in any one of SEQ. ID Nos. 4 or 5.

10. An isolated DNA comprising a sequence encoding 23 consecutive amino acids set forth in SEQ. ID No. 4.

11. The transgenic plant of claim 5, further comprising a recombinant DNA encoding a lytic peptide.

12. The transgenic plant of claim 11, wherein the lytic peptide is a thionin.

13. The transgenic plant of claim 6, further comprising a recombinant DNA encoding a lytic peptide.

14. The transgenic plant of claim 13, wherein the lytic peptide is a thionin.

15. A vector comprising the isolated DNA of claim 9.

16. A transgenic plant comprising the vector of claim 15.

17. The transgenic plant of claim 16, further comprising a recombinant DNA encoding a lytic peptide.

18. The transgenic plant of claim 17, wherein the lytic peptide is a thionin.

19. A vector comprising the isolated DNA of claim 10.

20. A transgenic plant comprising the vector of claim 19.

21. The transgenic plant of claim 20, further comprising a recombinant DNA encoding a lytic peptide.

22. The transgenic plant of claim 21, wherein the lytic peptide is a thionin.

23. A transgenic plant obtained by the method of claim 7.

* * * * *